(12) United States Patent
Hoge, II et al.

(10) Patent No.: US 6,689,915 B2
(45) Date of Patent: Feb. 10, 2004

(54) SYNTHESIS OF NON-$C_2$-SYMMETRIC BISPHOSPHINE LIGANDS AS CATALYSTS FOR ASYMMETRIC HYDROGENATION

(75) Inventors: Garrett Stewart Hoge, II, Ann Arbor, MI (US); Om Prakash Goel, Ann Arbor, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 87 days.

(21) Appl. No.: 10/083,923

(22) Filed: Feb. 27, 2002

(65) Prior Publication Data

US 2002/0143214 A1 Oct. 3, 2002

Related U.S. Application Data

(60) Provisional application No. 60/277,125, filed on Mar. 19, 2001.

(51) Int. Cl.$^7$ .................................................. C07F 9/50
(52) U.S. Cl. ............................................. 568/8; 568/17
(58) Field of Search ................................ 568/8, 13, 15, 568/16, 17

(56) References Cited

U.S. PATENT DOCUMENTS

| | | | | |
|---|---|---|---|---|
| 5,646,241 A | * | 7/1997 | Dershem et al. | ............ 528/422 |
| 6,194,593 B1 | * | 2/2001 | Imamoto et al. | ............ 556/136 |
| 6,376,715 B1 | * | 4/2002 | Newman et al. | ............... 568/17 |

FOREIGN PATENT DOCUMENTS

| | | |
|---|---|---|
| EP | 0 997 470 A1 | 5/2000 |
| JP | 11-80179 | 3/1999 |
| JP | 2000-256384 | 9/2000 |
| JP | 2000-319288 | 11/2000 |
| WO | WO 99 62917 A | 12/1999 |
| WO | WO 00 11008 A | 3/2000 |
| WO | WO 00 26220 A | 5/2000 |

OTHER PUBLICATIONS

CA:119:39370 abs of Inorganic Chemistry by Michos 32(8) pp 1370–5 1993.*
CA:134:311257 abs of Tetrahedron Letters by Ohashi et al 42(6) pp 1009–1101 2001.*
CA:120:152206 abs of Inorganic Chemistry by Bowmaker et al (23) pp 3593–3600 1993.*
CA:133:171445 abs of Dalton by Chatterjee et al (12) pp 1829–1830 2000.*
CA:120:243450 abs of Inorganic Chemistry by Gabbitas et al (22) pp 3271–6 1993.*
CA:91:122957 abs of Journal of Organic Chemistry by King et al 44(18) pp 3095–100 1979.*
CA:75:129903 abs of Inorganic Physical and Theoretical by Dawson et al (18) pp 2897–9 1971.*
CA:123:112179 abs of Journal of Chem Soc. Chem Comm. by Potyen et al (8) pp 849–51 1995.*
CA:97:110089 abs of Chemistry and Industry (5) pp 163–4 by Briggs et al 1982.*
CA;101:111030 abs of Tetrahedron Letts. by Kauffman et al 25(19) pp 1963–6 1984.*
Ramsden J.A. et al., "A chelating diphosphine with a single stereogenic phosphorus atom; Rp or Sp–(2–methoxyphenyl)–P–phenyl–P–(2'–diphenylphosphino)ethyl-phosphine", Tetrahedron, Asymmetry, vol. 5, No. 10, 1994, pp. 2033–2044.
Ohashi, Atsushi, et al, "A new synthetic route to unsymmetric P–chirogenic bisphosphine ligands", Tetrahedron Letters, 42 (2001); pp. 1099–1101.
Ohashi, Atsushi, et al, " Highly Enantioselective Hydrigenation of a–Dehydroamino Acids by Rhodium Complexes with New Unsymmetric P–Chirogenic Bisphosphine Ligands", Organic Letters, vol. 3, No. 3 (2001) pp. 373–375.
Ohashi, Atsushi, et al, : Unsymmetrical P–Chirogenic Bis(phosphane) Ligands: Their Preparation and Use in Rhodium–Catalyzed Asymmetric Hydrogenation, Eur. J. Org. Chem.(2002) pp. 2535–2546.

\* cited by examiner

*Primary Examiner*—Jean F. Vollano
(74) *Attorney, Agent, or Firm*—Francis J. Tinney; Matthew J. Russo

(57) ABSTRACT

Non-$C_2$-symmetric bisphospholane ligands and methods for their preparation are described. Use of metal/non-$C_2$-symmetric bisphospholane complexes to catalyze asymmetric transformation reactions to provide high enantiomeric excesses of formed compounds is also described.

17 Claims, 9 Drawing Sheets

R = t-butyl, isopropyl, adamantyl, (1,1)-dimethylpropane,
(1,1)-diethylbutane, c-$C_5H_9$, or c-$C_6H_{11}$
$R_1$ = methyl, ethyl, isopropyl, cyclohexyl, or any alkyl
Ms = mesylate

SYNTHESIS OF NON-C$_2$-SYMMETRIC BISPHOSPHINE LIGANDS AS CATALYSTS FOR ASYMMETRIC HYDROGENATION

CROSS-REFERENCE TO RELATED APPLICATION

This application claims the benefit of U.S. Provisional Patent Application No. 60/277,125, filed Mar. 19, 2001.

FIELD OF THE INVENTION

This invention relates to non-C$_2$-symmetric bisphosphine (BisP) ligands and a method for their preparation. In addition, this invention relates to forming metal/bisphosphine complexes that catalyze asymmetric transformation reactions to generate high enantiomeric excesses of formed compounds. The invention also relates to a method for preparing BisP.

BACKGROUND OF THE INVENTION

A growing trend in the pharmaceutical industry is to market chiral drugs in enantiomerically pure form to provide desired positive effects in humans. Production of enantiomerically pure compounds is important for several reasons. First, one enantiomer often provides a desired biological function through interactions with natural binding sites, but another enantiomer typically does not have the same function or effect. Further, it is possible that one enantiomer has harmful side effects, while another enantiomer provides a desired positive biological activity. To meet this demand for chiral drugs, many approaches for obtaining enantiomerically pure compounds have been explored such as diastereomeric resolution, structural modification of naturally occurring chiral compounds, asymmetric catalysis using synthetic chiral catalysts and enzymes, and the separation of enantiomers using simulated moving bed (SMB) technology.

Asymmetric catalysis is often the most efficient method for the synthesis of enantiomerically enriched compounds because a small amount of a chiral catalyst can be used to produce a large quantity of a chiral target molecule. Over the last two decades, more than a half-dozen commercial industrial processes have been developed that use asymmetric catalysis as the key step in the production of enantiomerically pure compounds with a tremendous effort focused on developing new asymmetric catalysts for these reactions (Morrison J. D., ed. *Asymmetric Synthesis*, New York: Academic Press, 1985:5; Bosnich B., ed. *Asymmetric Catalysis*, Dordrecht, Netherlands: Martinus Nijhoff Publishers, 1986; Brunner H. *Synthesis*, 1988:645; Noyori R., Kitamura M. In Scheffold R., ed. *Modern Synthetic Methods*, Berlin Hedelberg: Springer-Verlag, 1989;5: 115; Nugent W. A., RajanBabu T. V., Burk M. J. *Science*, 1993;259:479; Ojima I., ed. *Catalytic Asymmetric Synthesis*, New York: VCH, 1993; Noyori R. *Asymmetric Catalysis In Organic Synthesis*, New York: John Wiley & Sons, Inc, 1994).

Chiral phosphine ligands have played a significant role in the development of novel transition metal catalyzed asymmetric reactions to produce enantiomeric excess of compounds with desired activities. The first successful attempts at asymmetric hydrogenation of enamide substrates were accomplished in the late 1970s using chiral bisphosphines as transition metal ligands (Vineyard B. D., Knowles W. S., Sabacky M. J., Bachman G. L., Weinkauff D. J. J. *Am. Chem. Soc.* 1977;99(18):5946–52; Knowles W. S., Sabacky M. J., Vineyard B. D., Weinkauff D. J. *J. Am. Chem. Soc.* 1975;97(9):2567–8).

Since these first published reports, there has been an explosion of research geared toward the synthesis of new chiral bisphosphine ligands for asymmetric hydrogenations and other chiral catalytic transformations (Ojima I., ed. *Catalytic Asymmetric Synthesis*, New York: VCH Publishers, Inc, 1993; Ager D. J., ed. *Handbook of Clinical Chemicals*, Marcel Dekker, Inc, 1999). Highly selective rigid chiral phospholane ligands have been used to facilitate these asymmetric reactions. For example, phospholane ligands are used in the asymmetric hydrogenation of enamide substrates and other chiral catalytic transformations.

BPE, Duphos, and BisP ligands are some of the most efficient and broadly useful ligands developed for asymmetric hydrogenation to date (Burk M. J. *Chemtracts* 1998; 1(1 1):787–802 (CODEN: CHEMFW ISSN:1431–9268. CAN 130:38423; AN 1998:698087 CAPLUS); Burk M. J., Bienewald F., Harris M., Zanotti-Gerosa A. *Angew Chem.*, Int. Ed. 1998;37(13/14):1931–1933; Burk, M. J., Casy G., Johnson N. B. *J. Org. Chem.* 1998;63(18):6084–6085; Burk M. J., Kalberg C. S., Pizzano A. *J. Am. Chem. Soc.* 1998;120 (18):4345–4353; Burk M. J., Harper T., Gregory P., Kalberg C. S. *J. An. Chem. Soc.* 1995;117(15):4423–4424; Burk M. J., Feaster J. E., Nugent W. A., Harlow R. L. *J. Am. Chem. Soc.* 1993;115(22):10125–10138; Nugent W. A., RajanBabu T. V., Burk M. J. *Science* (Washington, DC 1883-) 1993;259 (5094):479–483; Burk M. J., Feaster J. E., Harlow R. L. *Tetrahedron: Asymmetry* 1991;2(7):569–592; Burk M J. *J. Am. Chem. Soc.* 1991;113(22):8518–8519; Imamoto T., Watanabe J., Wada Y., Masuda H., Yamada H., Tsuruta H. et al. *J. Am. Chem. Soc.* 1998; 120(7):1635–1636; Zhu G, Cao P, Jiang Q, Zhang X. *J. Am. Chem. Soc.* 1997; 119(7): 1799–1800). For example, a Rhodium/Duphos complex can be used to selectively form (S)-(+)-3-(aminomethyl)-5-methylhexanoic acid, known as pregabalin, which is used as an anti-seizure drug. The S-enantiomer, which is produced in an enantiomeric excess, is preferred because it shows better anticonvulsant activity than the R-enantiomer (Yuen et al., *Bioorganic & Medicinal Chemistry Letters* 1994;4:823).

The success of BPE, DuPhos, and BisP transition metal complexes in asymmetric hydrogenations is derived from many factors. For example, substrate to catalyst ratios of up to 50,000/1 have been demonstrated. Also, high rates of substrate conversion to product using low hydrogen pressures have been observed with catalysts made from these ligands.

BPE, Duphos, and BisP have shown high enantioselectivities in numerous asymmetric reactions. Improved reaction of BPE, Duphos, and BisP is attributed to, among other factors, rigidity in their C$_2$-symmetric structure. If the spatial area of a metal/phosphine ligand structure, such as BisP, is divided into four quadrants, as shown in FIG. 1, alternating hindered and unhindered quadrants are formed.

This structural feature creates areas of hindrance in the BisP/metal complexes and produces desired stereochemical results in asymmetric hydrogenation reactions. However, there are a variety of reactions in which only modest enantioselectivity has been achieved with these ligands. While high selectivity has been observed in many reactions using these chiral diphosphine ligands, there are many reactions where these ligands are not very efficient in terms of activity and selectivity. Further, there are many disadvantages associated with these ligands, which limits their application.

For example, multiple chiral centers in these ligands increases the difficulty in synthesis of these compounds.

Further, the multiple chiral centers could increase the cost associated with forming the ligands.

High enantioselectivities have been observed in asymmetric hydrogenation for a narrow range of substrates, such as enamides, enol esters, and succinates. Many of these successful results have been obtained using optically pure $C_2$-symmetric rhodium-phosphine complexes as hydrogenation catalysts. Therefore, $C_2$-symmetry has become a popular characteristic in the design of chiral ligands that are used to make these complexes. Unique to the substrates for which asymmetric hydrogenation has been successful is an olefin and a carbonyl group which are separated by one atom. During asymmetric hydrogenation, the olefin and the carbonyl bind to the metal center in a well-defined conformation. This is thought to be of consequence in an asymmetric hydrogenation.

$C_2$-symmetric bisphosphines, such as BisP, have been synthesized and used in asymmetric catalysis, as shown in FIG. 2 (Imamoto, T., Watanabe J., Wada Y., Masuda H., Yamada H., Tsuruta I-I., Matsukawa S., Yamaguchi K. J Am. Chem. Soc. 1998;120(7):1635–1636). A proton from one of the methyl groups of t-butyldimethyl phosphine is selectively deprotonated with a chiral base, such as s-BuLi and (−)-sparteine, and then the resulting anion couples with itself in the presence of copper(II) chloride to provide the bisphosphine borane protected ligand, in about 40% yield and >99% enantiomeric excess after recrystallization. The rhodium complex of BisP is known to give high enantiomeric excess in hydrogenation reactions for a variety of substrates. For instance, the rhodium-BisP catalyst hydrogenates x-N-acetylmethylacrylate to produce 98% enantiomeric excess (Imamoto T. et al., supra., 1998).

A drawback to the synthesis of the BisP ligand in FIG. 2 is that only one antipode of sparteine is available in nature, and therefore, only one enantiomer of the ligand (the S,S isomer) can be synthesized via this route.

Basic research has been done by a variety of groups in the late 1970s on the mechanism and origin of enantioselectivity of asymmetric hydrogenation reactions which result in high enantiomeric excess (Alcock N. W., Brown J. M.; Derome A. E., Lucy A. R. J. Chem. Soc. Chem. Comm. 1985:575; Brown J. M., Chaloner P. A., Morris G. A. J. Chem. Soc. Chem. Comm. 1983:664; Halpern J. Science 1982;217,401; Brown J. M., Chaloner P. A. J. Chem. Soc. Chem. Comm. 1980;344). The 3-dimensional structure of a $C_2$-symmetric complex like the rhodium complex of BisP has four quadrants that alternate hindered and unhindered, as shown in FIG. 1.

Ligand and metal/ligand complexes are needed that can further improve the production of enantiomerically active forms of compounds. Thus, there is a need to develop methods for the production of and to synthesize compounds that reduce the number of chiral centers on a molecule and through prohibitive substituents on the ligand improve enantioselectivity in asymmetric reactions.

SUMMARY OF THE INVENTION

The present invention provides for non-$C_2$-symmetric bisphosphine ligands. Non-$C_2$ bisphosphine ligands when complexed with a metal, serve as catalysts in asymmetric hydrogenation reactions to form enantiomerically enriched compounds. One non-$C_2$-symmetric bisphosphine is represented by the general Formula I:

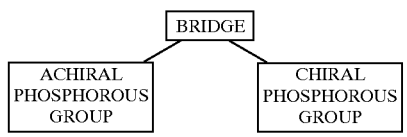

wherein:

the achiral phosphorous group includes at least one achiral phosphorous atom having one bond to each of two identical atoms other than the bridge;

the chiral phosphorous group comprises at least one phosphorous atom, wherein the at least one phosphorous atom is chiral or the at least one phosphorous atom is bonded to a chiral substituent; and the Bridge is a —$(CH_2)_n$— where n is an integer from 1 to 12; a 1,2-divalent phenyl; or a 1,2-divalent substituted phenyl.

Another non-$C_2$-symmetric bisphosphine compound of present invention has the general Formula II:

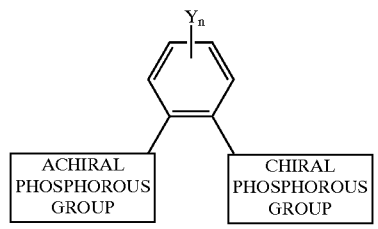

wherein:

the achiral phosphorous group includes at least one achiral phosphorous atom having one bond to each of two identical atoms other than the bridge;

the chiral phosphorous group comprises at least one phosphorous atom, wherein the at least one phosphorous atom is chiral or the at least one phosphorous atom is bonded to a chiral substituent; and each Y is independently halogen, alkyl, alkoxy, aryl, aryloxy, nitro, amino, vinyl, substituted vinyl, alkynyl, or sulfonic acid, and n is an integer from 0 to 4 equal to the number of unsubstituted aromatic ring carbons.

Another aspect of the invention is directed to the method for forming P-chiral bisphosphine ligands. Compounds used as synthons during the synthesis of non-$C_2$-symmetric bisphosphine ligands include compounds with the Formulas III, IV, V, and VI:

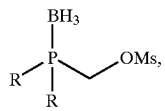

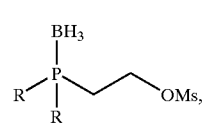

-continued

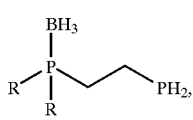
V

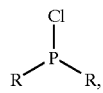
VI wherein R is t-butyl, isopropyl, adamantyl, (1,1-dimethylpropane), (1,1-diethylbutane) c-$C_5H_9$, or c-$C_6H_{11}$; and Ms is mesylate.

Another aspect of the invention is directed to methods for forming non-$C_2$-bisphosphine ligands. The methods include preparing compounds of the general structural Formulas I and II, as shown in FIG. 4–FIG. 12.

Another compound of the present invention has the general Formula VIII:

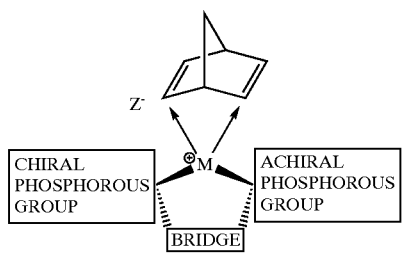
VIII wherein:
the achiral phosphorous group includes at least one achiral phosphorous atom having one bond to each of two identical atoms other than the bridge;
the chiral phosphorous group comprises at least one phosphorous atom, wherein the at least one phosphorous atom is chiral or the at least one phosphorous atom is bonded to a chiral substituent;
a Bridge is a —$(CH_2)_n$— where n is an integer from 1 to 12; a 1,2-divalent phenyl; or a 1,2-divalent substituted phenyl;
M is a transition metal, an actinide, or a lanthanide; and
Z is $BF_4$, $PF_6$, $SbF_6$, OTf, or $ClO_4$.

Yet another aspect of the invention is directed to forming enantiomeric excesses of compounds catalyzed with the metal/non-$C_2$-symmetric bisphosphine complexes in asymmetric reactions.

DETAILED DESCRIPTION OF THE INVENTION

Figure 1:
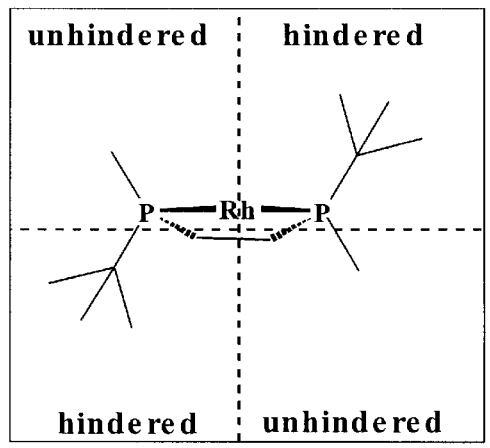
FIG. 1 depicts a spatial arrangement of a metal/phosphine ligand.
Figure 2:
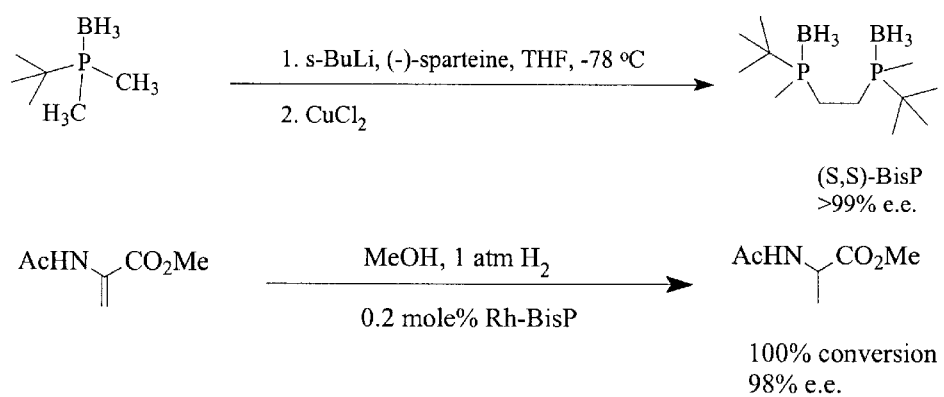
FIG. 2 shows representative schemes for preparing $C_2$-symmetric bisphosphines, such as BisP, and for using $C_2$-symmetric bisphosphines in asymmetric catalysis.

The present invention is applicable to the synthesis of non-$C_2$-symmetric bisphosphine ligands for use in metal/non-$C_2$-symmetric bisphosphine complexes for asymmetric catalysis. In particular, the present invention is directed to reacting the metal/non-$C_2$-symmetric bisphosphine complexes to produce enantiomeric excesses of compound in asymmetric hydrogenation syntheses. While the present invention is not so limited, an appreciation of various aspects of the invention will be gained through a discussion of the examples provided below.

For the purpose of this application, the "corresponding enantiomer" means that if a compound includes a stereochemical configuration designated as R, the corresponding enantiomer is the S configuration. If a compound has an S configuration, the corresponding enantiomer is the R configuration. If a compound has a stereochemical configuration of 1R,2S, the "corresponding enantiomer" is the 1S,2R compound. Similarly, if a compound has an 1S,2R configuration, the "corresponding enantiomer" is the 1R,2S compound. If a P-chiral compound has an 1S,2S configuration, the "corresponding enantiomer" is the 1R,2R compound. If a compound has an 1R,2R configuration, the "corresponding enantiomer" is the 1S,2S compound.

For the purpose of this application, a high level of enantioselectivity means a hydrogenation that yields a product of greater than or equal to about 80%, preferably, greater than or equal to about 90% enantiomeric excess (abbreviated e.e.).

Enantiomeric excess is defined as the ratio (%R–%S)/(%R+%S)×100, where %R is the percentage of R enantiomer and %S is the percentage of S enantiomer in a sample of optically active compound. For the purpose of this application, by a "compound with a high degree of enantiomeric purity," or a "compound of high enantiomeric purity" is meant a compound that exhibits enantiomeric excess to the extent of greater than or equal to about 90%, preferably, greater than or equal to about 95% enantiomeric excess (abbreviated e.e.).

Non-$C_2$-Symmetric Bisphosphines

The present invention provides novel non-$C_2$-symmetric bisphosphine substituted compounds of the general Formula 1:

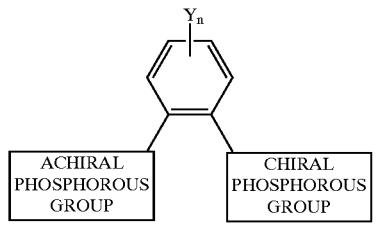

I wherein:
   the achiral phosphorous group includes at least one achiral phosphorous atom having one bond to each of two identical atoms other than the bridge;
   the chiral phosphorous group comprises at least one phosphorous atom, wherein the at least one phosphorous atom is chiral or the at least one phosphorous atom is bonded to a chiral substituent; and
   the Bridge is a —(CH$_2$)$_n$— where n is an integer from 1 to 12; a 1,2-divalent phenyl; or a 1,2-divalent substituted phenyl.

Another non-C$_2$-symmetric bisphosphine compound of present invention has the general Formula II:

II wherein:
   the achiral phosphorous group includes at least one achiral phosphorous atom having one bond to each of two identical atoms other than the bridge;
   the chiral phosphorous group comprises at least one phosphorous atom, wherein the at least one phosphorous atom is chiral or the at least one phosphorous atom is bonded to a chiral substituent; and
   each Y is independently halogen, alkyl, alkoxy, aryl, aryloxy, nitro, amino, vinyl, substituted vinyl, alkynyl, or sulfonic acid, and n is an integer from 0 to 4 equal to the number of unsubstituted aromatic ring carbons.

The term "alkyl", as used in this application, includes a straight or branched saturated aliphatic hydrocarbon chain, such as, for example, methyl, ethyl, propyl, isopropyl (1-methylethyl), butyl, tert-butyl (1,1-dimethylethyl), and the like.

The term "aryl" group, as used in this application, includes an aromatic hydrocarbon group, including fused aromatic rings, such as, for example phenyl and naphthyl. Such groups may be unsubstituted or substituted on the aromatic ring by, for example, an alkoxy group of 1 to 4 carbon atoms, an amino group, a hydroxy group, or an acetyloxy group.

The term "aralkyl" group, as used in this application, includes an aromatic hydrocarbon group, including fused aromatic rings, such as for example, phenyl and naphthyl, bonded to an alkyl group with the alkyl bonded to the pholane ring. The aromatic hydrocarbon group may be unsubstituted or substituted (ring substituted aralkyl) by, for example, an alkoxy group of 1 to 4 carbon atoms, an amino group, a hydroxy group, or an acetyloxy group.

The term "LAH," as used in this application, is defined as lithium aluminum hydride.

Achiral phosphorous groups include, but are not limited to, the following:

wherein R is t-butyl, isopropyl, adamantyl, (1,1-dimethylpropane), (1,1-diethylbutane), c-C$_5$H$_9$, or c-C$_6$H$_{11}$.

Chiral phosphorous groups include, but are not limited to, the following and their corresponding enantiomers:

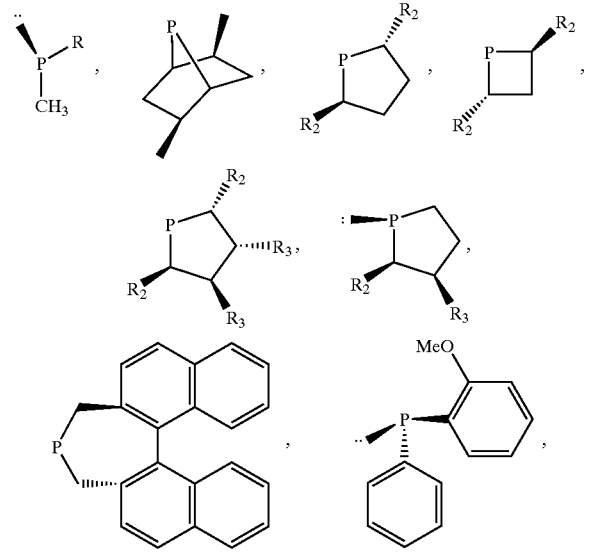

wherein:
   R is t-butyl, isopropyl, adamantyl, (1,1-dimethylpropane), (1,1-diethylbutane), c-C$_5$H$_9$, or c-C$_6$H$_{11}$;
   R$_2$ is methyl, ethyl, isopropyl, cyclohexyl, benzyl, a ring substituted benzyl, an aryl, or a ring substituted aryl; and
   R$_3$ is OBn, OH, suiphonate, or hydrogen.

A preferred R group for the achiral phosphorous groups of compounds of the general Formula I is t-butyl. Examples of other preferred non-C$_2$-synimetric bisphosphine ligands of the general Formula I include, but are not limited to, those compounds in which R is isopropyl, adamantyl, (1,1-dimethylpropane), (1,1-diethylbutane), c-C$_5$H$_9$, or c-C$_6$H$_{11}$ and their corresponding enantiomers.

The non-C$_2$-symmetric bisphosphine substituted compound, 1-(di-tert-butyl-phosphanyl)-((R)-2-tert-butyl-methyl-phosphanyl)ethane is represented by the Formula Ia:

Ia

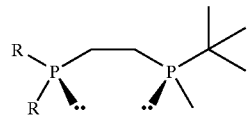

wherein R is t-butyl. In other embodiments, R is isopropyl, adamantyl, (1,1-dimethylpropane), (1,1-diethylbutane), c-C$_5$H$_9$, or c-C$_6$H$_{11}$.

The non-C$_2$-symmetric bisphosphine substituted compound, 1-((S)-2,2'-phosphanyl-1,1'-binaphthyl)-2-((R)-2-tert-butyl-methyl-phosphanyl)ethane is represented by the Formula Ib:

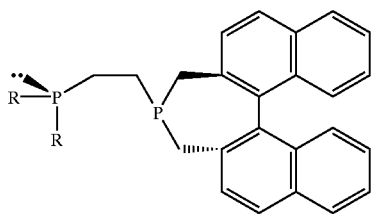

Ib wherein R is t-butyl.

The non-$C_2$-symmetric bisphosphine substituted compound, 1-((R)-2-tert-butyl-methyl-phosphanyl)-2-((R,R)-2,5-dialkylphosphanyl)ethane is represented by the Formula Ic:

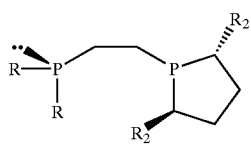

Ic wherein R is t-butyl, and $R_2$ is alkyl.

The non-$C_2$-symmetric bisphosphine substituted compound, 1-((R)-2-tert-butyl-methyl-phosphanyl)-2-((R,R)-2,5-dialkylphosphanyl)benzene is represented by the Formula IIa:

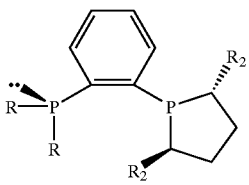

IIa wherein R is t-butyl, and $R_2$ is alkyl.

Compounds of the general Formulas Ia, Ib, and Ic include the corresponding enantiomer of the compound shown in the structural formulas.

The bisphosphine compounds of Formula I and II of the present invention are useful as transition metal ligands in asymmetric catalysis. The use of these ligands to form transition metal catalysts results in a high level of enantioselective and stereochemical control in the catalyzed hydrogenation of unsaturated substrates.

Compounds I and II include one to three chiral centers instead of the four chiral centers that are found in molecules such as Duphos. Ligands displaying the structural motif of Ia do not necessarily have to contain bulky groups on phosphorous that are the same. In other words, as long as there are three sterically hindered quadrants in the metal-ligand complex, the desired effect in asymmetric transformations will be achieved.

Several intermediate synthon compounds can be used to form non-$C_2$-symmetric compounds, such as those with the general Formula I. This invention further comprises the use or synthesis of synthons with the Formulas III, IV, V, and VI:

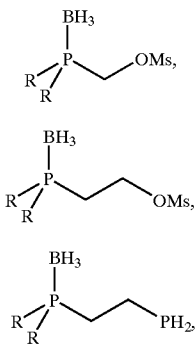

III

IV

V

VI wherein R is t-butyl, isopropyl, adamantyl, (1,1-dimethylpropane), (1,1-diethylbutane), c-$C_5H_9$, or c-$C_6H_{11}$; and Ms is mesylate.

The above bisphospholane compounds of Formulas I, II, and their corresponding enantiomers can be complexed with any of the transition metals as well as the lanthanides and actinides. Such complexes are formed by methods known in the art. Another compound of the present invention includes the metal/P-chiral phospholane complex with the general structural Formula VIII and its corresponding enantiomer:

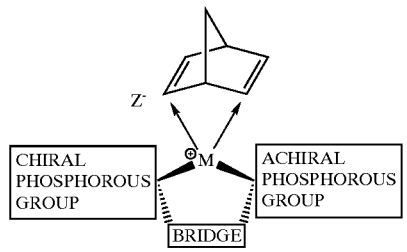

VIII wherein:
the achiral phosphorous group includes at least one achiral phosphorous atom having one bond to each of two identical atoms other than the bridge;
the chiral phosphorous group comprises at least one phosphorous atom, wherein the at least one phosphorous atom is chiral or the at least one phosphorous atom is bonded to a chiral substituent;
a Bridge is a —$(CH_2)_n$— where n is an integer from 1 to 12; a 1,2-divalent phenyl; or a 1,2-divalent substituted phenyl;
M is a transition metal, an actinide, or a lanthanide; and
Z is $BF_4$, $PF_6$, $SbF_6$, OTf, or $ClO_4$.

Preferred transition metal complexes of the present invention are those including the above described preferred compounds complexed with rhodium.

Synthesis of non-$C_2$ Bisphosphines

Figure 3:
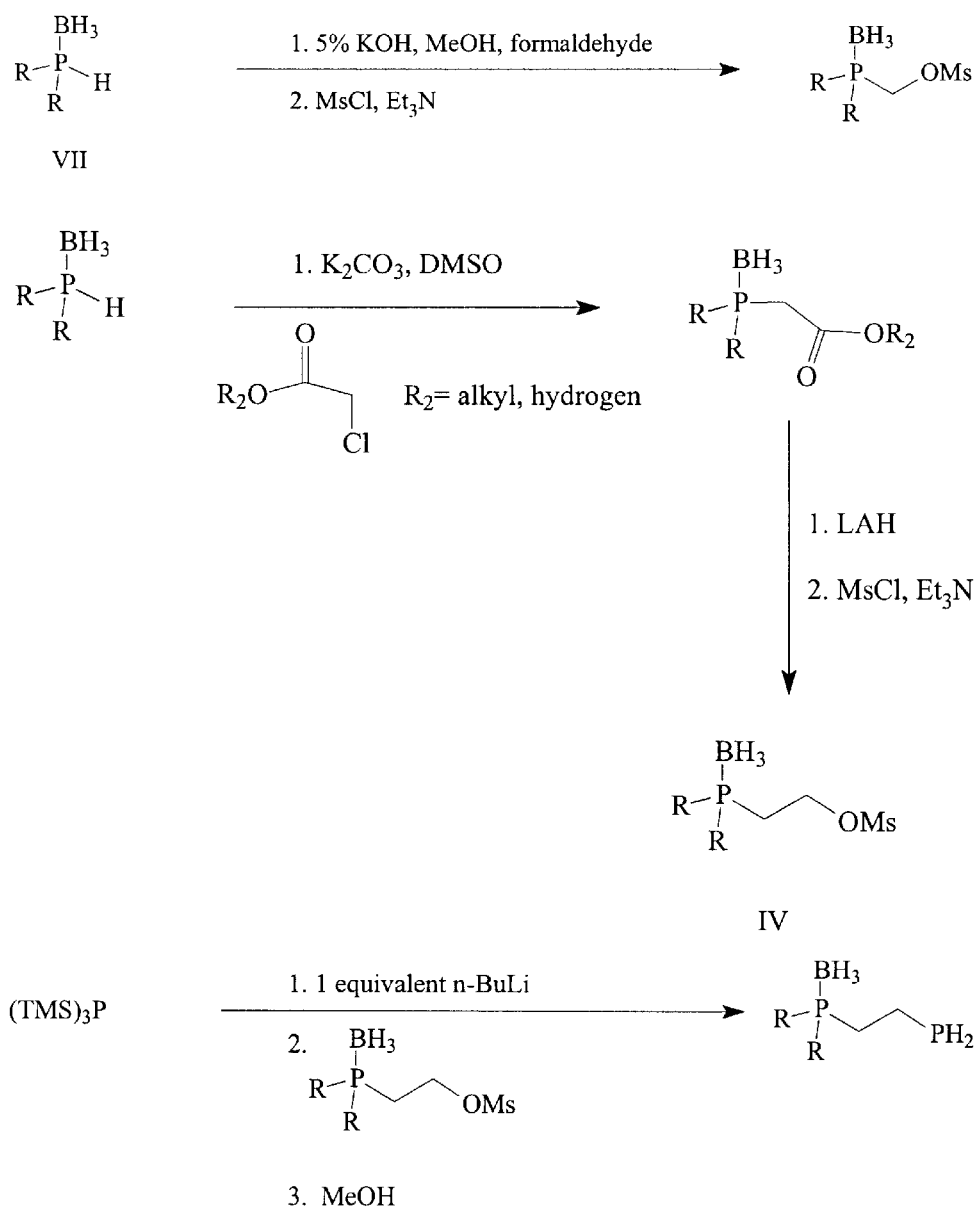
FIG. 3 shows schemes for preparing synthons that can be used to prepare non-$C_2$-symmetric borane-protected ligands.
Figure 4:
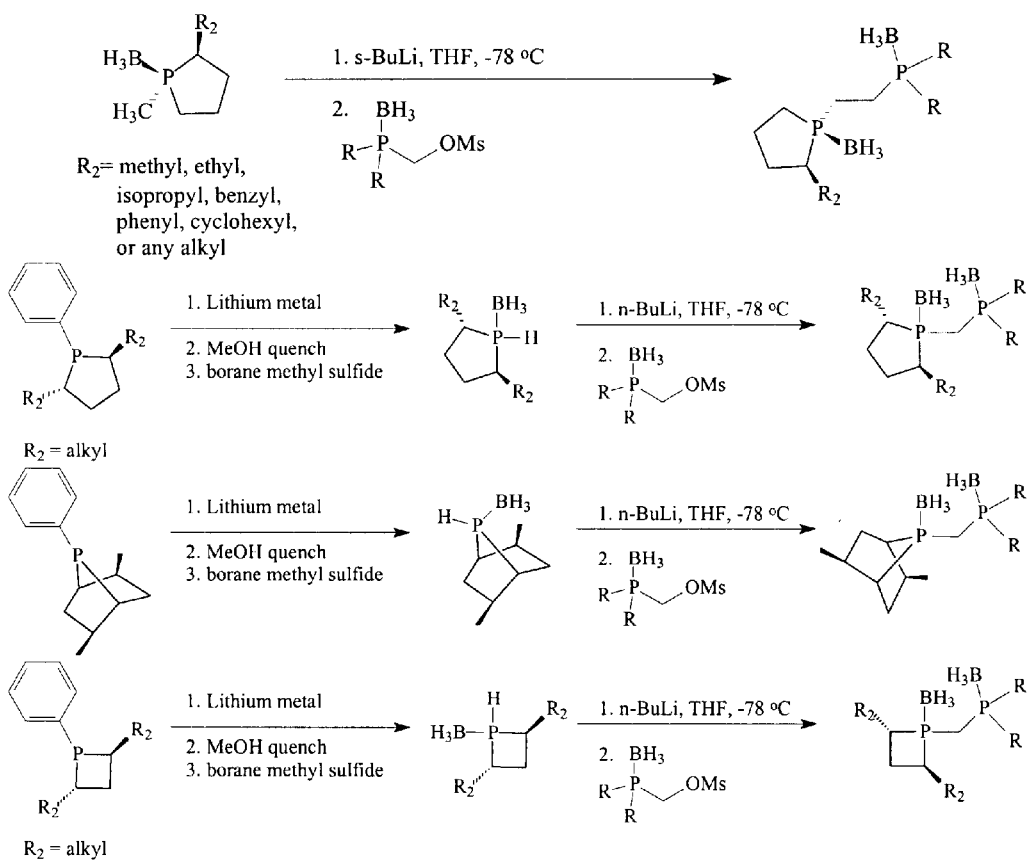
FIG. 4 shows schemes for preparing non-$C_2$-symmetric ligands using synthon III.
Figure 5:
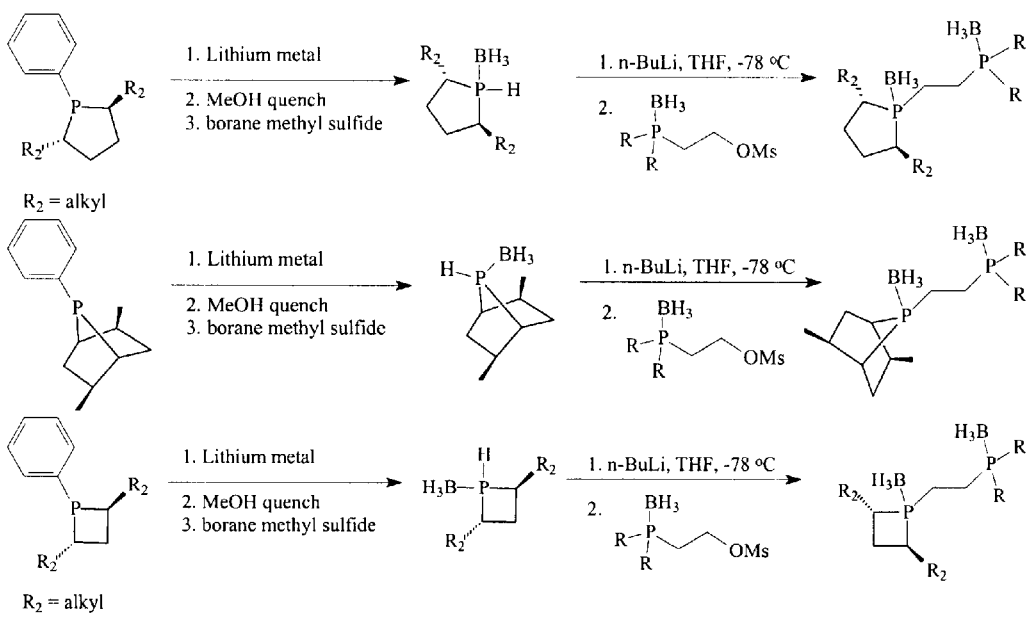
FIG. 5 shows schemes for preparing non-$C_2$-symmetric ligands using synthon IV.
Figure 6:
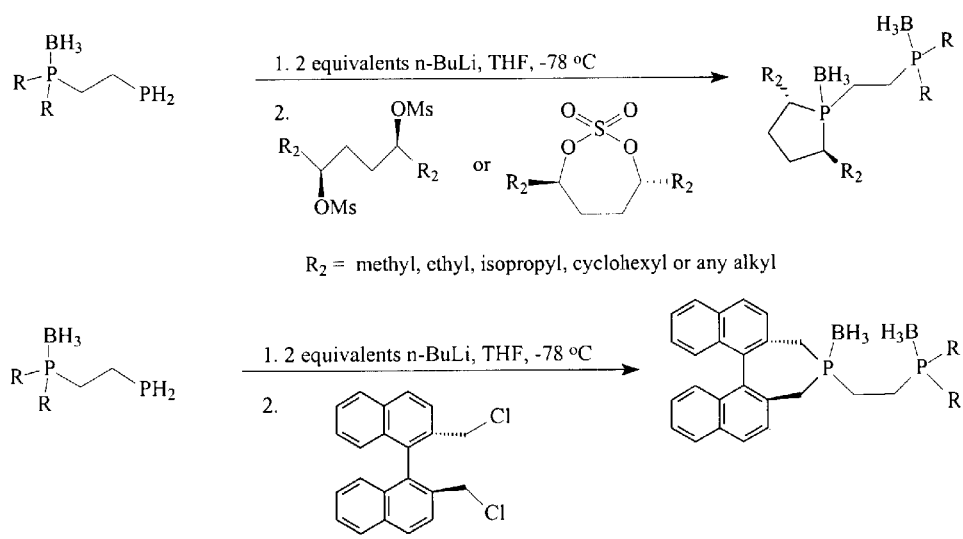
FIG. 6 shows schemes for preparing non-$C_2$-symmetric ligands using synthon V.
Figure 7:
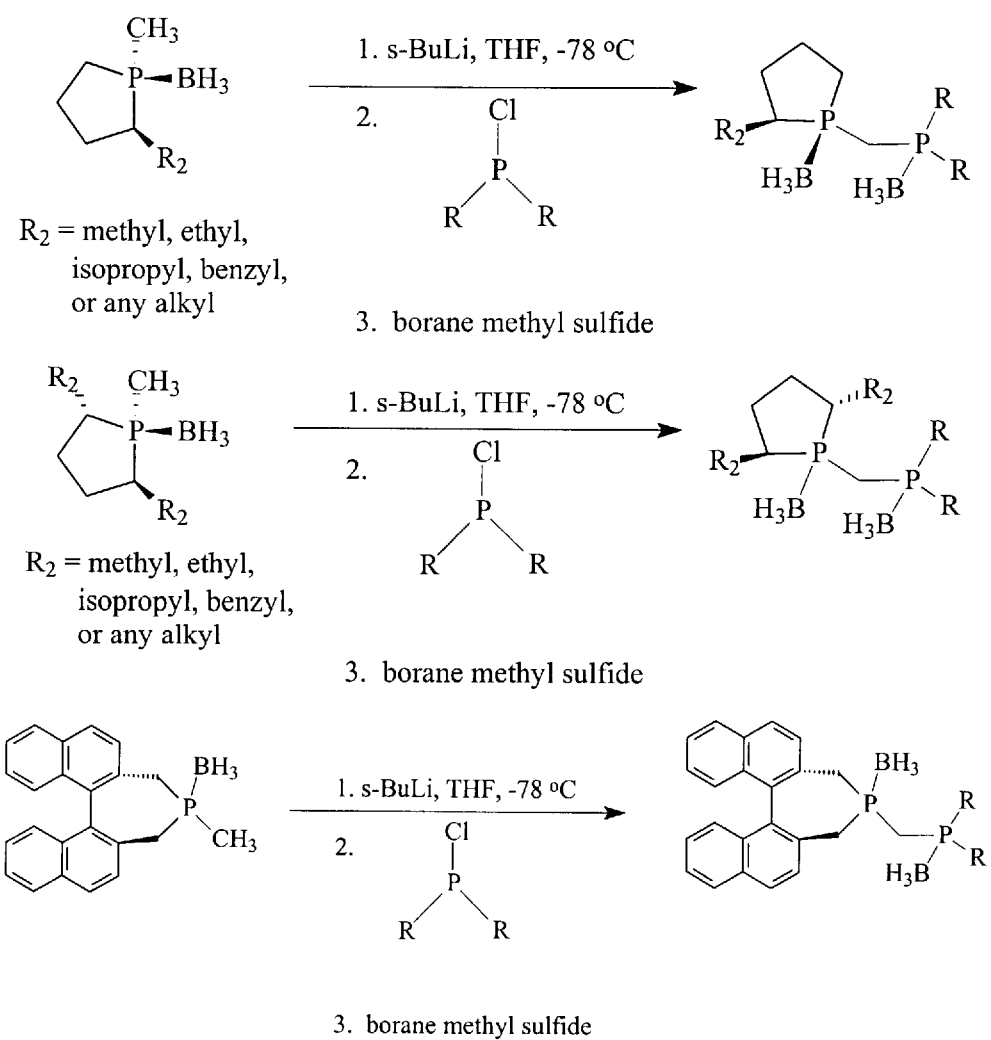
FIG. 7 shows schemes for preparing non-$C_2$-symmetric ligands using synthon VI.
Figure 8:
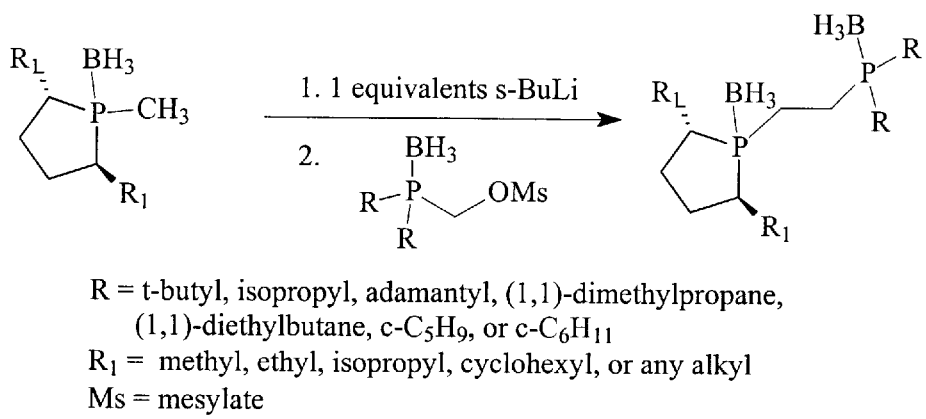
FIG. 8 shows a scheme for preparing non-$C_2$-symmetric ligands using synthon VII.

The synthesis the non-$C_2$ borane-protected ligands can be formed through synthons that are formed as shown in FIG. 3. For the synthons shown R is t-butyl, isopropyl, adamantyl, (1,1)-dimethylpropane, (1,1-diethylbutane), c-$C_5H_9$, or c-$C_6H_{11}$; and Ms is mesylate.

An additional synthon is a compound with the formula:

VI wherein R is t-butyl, isopropyl, adamantyl, (1,1)-dimethylpropane, (1,1-diethylbutane), c-$C_5H_9$, or c-$C_6H_{11}$. The above synthons can be used in a variety of reactions to form non-$C_2$-symmetric ligands as shown in FIG. 4–FIG. 8. In each of the schemes shown in FIG. 4–FIG. 8, R is t-butyl, isopropyl, adamantyl, (1,1)-dimethylpropane, (1,1-diethylbutane), c-$C_5H_9$, or c-$C_6H_{11}$, and Ms is mesylate.

Figure 9:
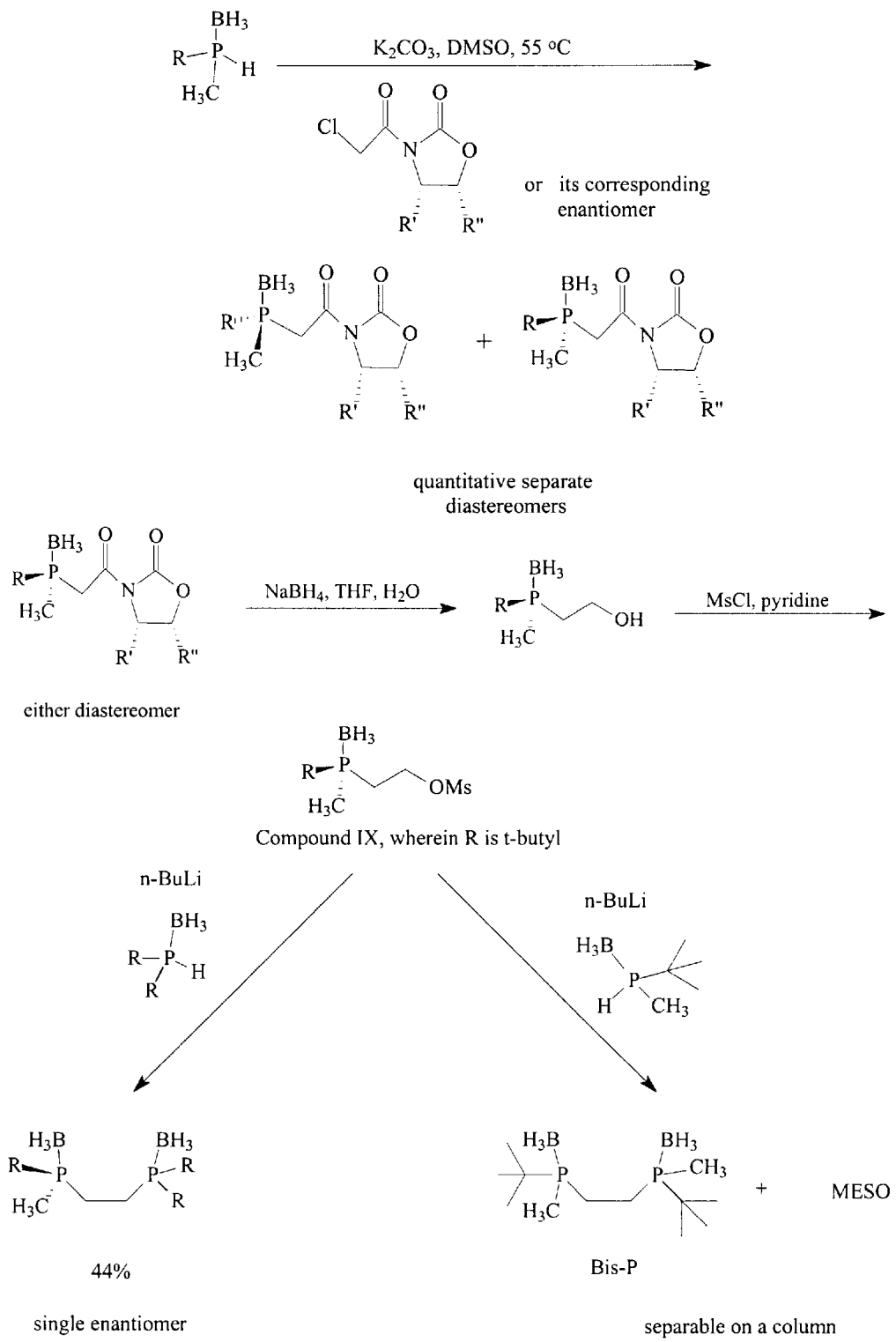
FIG. 9 shows a scheme for preparing compounds of Formula Ia.

FIG. 9 shows a method of synthesis to compound Ia. In the scheme shown in FIG. 9, R is t-butyl, isopropyl, adamantyl, (1,1)-dimethylpropane, (1,1-diethylbutane), c-$C_5H_9$, or c-$C_6H_{11}$; Ms is mesylate; R' is methyl, benzyl, aryl, isopropyl; and R" is H, methyl, benzyl, aryl, or isopropyl.

One method includes reacting (+/−)-tert-butyl-methyl-phosphane borane as a starting material. This primary phosphine is made via a one-pot procedure starting from dichloromethylphosphine, reacting with dimethylsulfide-borane, t-butyl magnesium chloride, and then LAH. (+/−)-tert-butyl-methyl-phosphane borane is reacted with a chiral auxiliary that includes $K_2CO_3$, DMSO, and N-chloroacetyl-(S)-(−)-4-benzyl-2-oxazolidinone at 55° C. to form a mixture of diastereomers (S)-4-benzyl-3-[2-((R)-tert-butyl-methyl-phosphanyl)-ethanoyl]-oxazolidin-2-one and (S)-4-benzyl-3-[2-((S)-tert-butyl-methyl-phosphanyl)-ethanoyl]-oxazolidin-2-one in quantitative yield. These diastereomers can be separated either by column chromatography or via recrystallization.

Each diastereomer can then be reduced with $NaBH_4$ to remove the chiral auxiliary and form either enantiomer of the alcohol, 2-(tert-butyl-methyl-phosphanyl)-ethanol, as shown in FIG. 9. The alcohol is then reacted with mesylate chloride and pyridine to form the compound IX. The corresponding enantiomer of compound IX can also be formed by choosing the opposite diastereomer. Compound IX can then be reacted with a mixture of n-butyl lithium and compound VII. Alternatively, compound IX can then be reacted with a mixture of n-butyl lithium and t-butylmethylphosphine borane to form Bis-P and a meso product.

Figure 10:
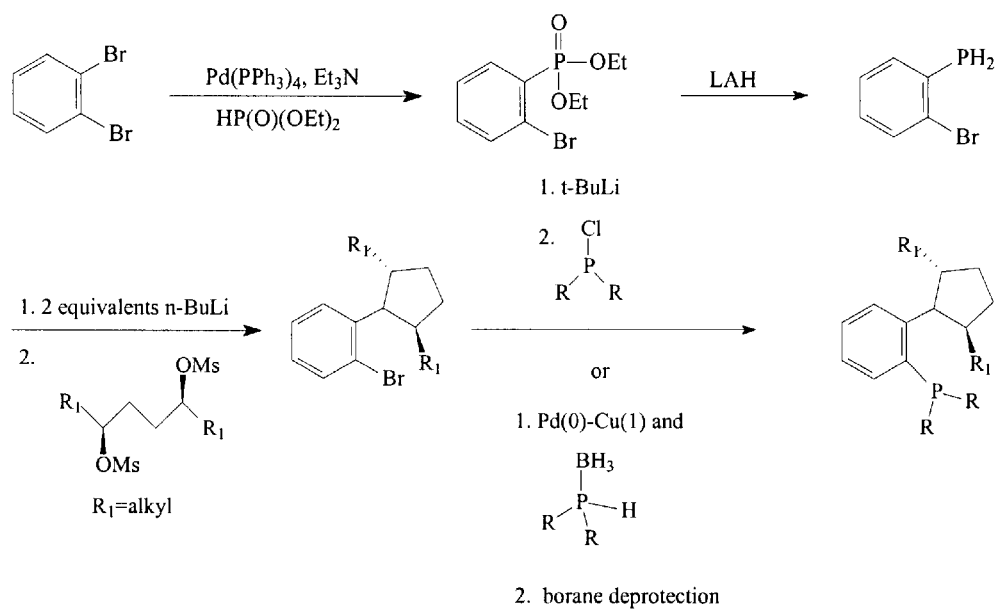
FIG. 10 shows a scheme for preparing compounds of Formula IIa.

The compound with the general Formula IIa can be synthesized via the route shown in FIG. 10, wherein R is t-butyl, isopropyl, adamantyl, (1,1)-dimethylpropane, (1,1-diethylbutane), c-$C_5H_9$, or c-$C_6H_{11}$, and Ms is mesylate.

Figure 11:
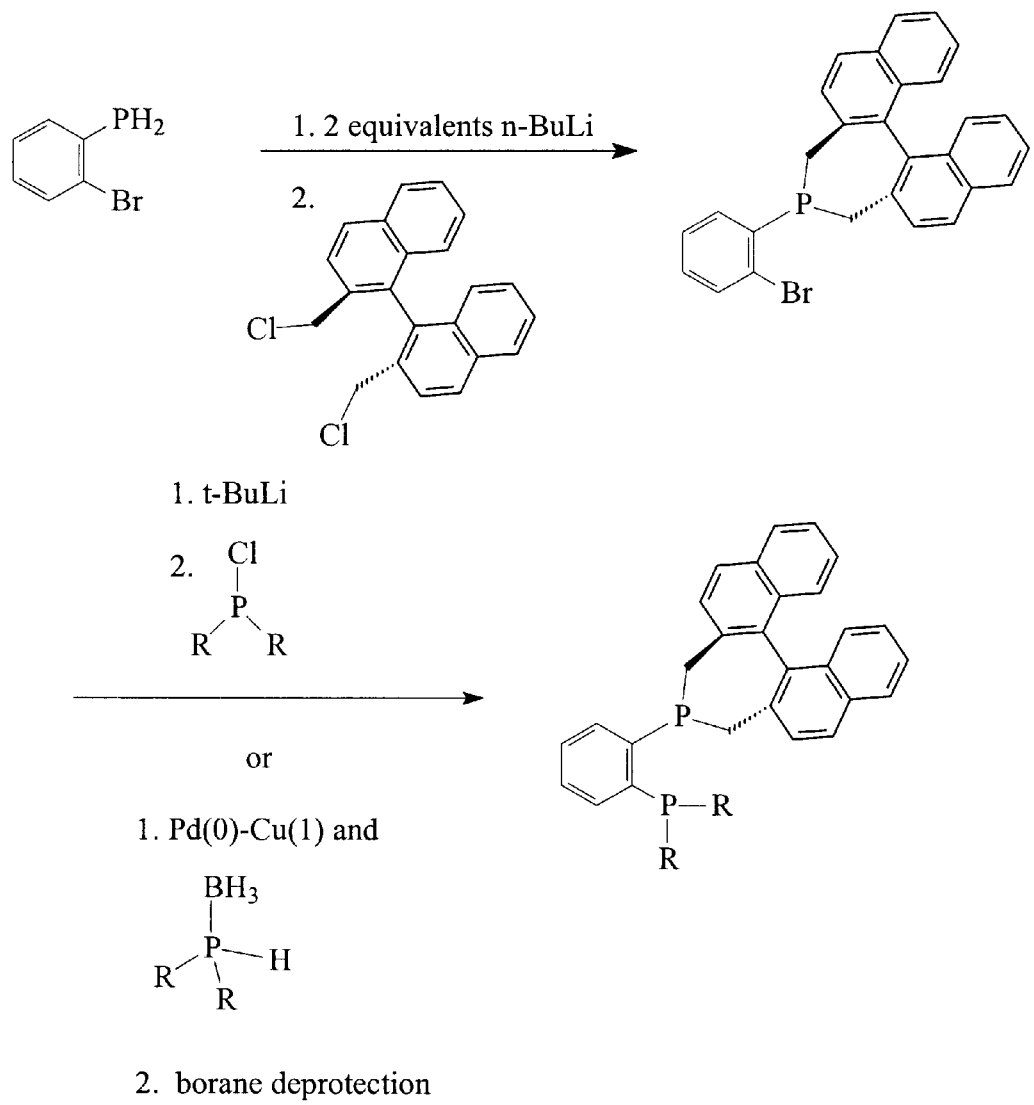
FIG. 11 shows a scheme for preparing compounds of Formula Ib.

The compound with the general Formula Ib can be synthesized via the route shown in FIG. 11, wherein R is t-butyl, isopropyl, adamantyl, (1,1)-dimethylpropane, (1,1-diethylbutane), c-$C_5H_9$, or c-$C_6H_{11}$.

Figure 12:
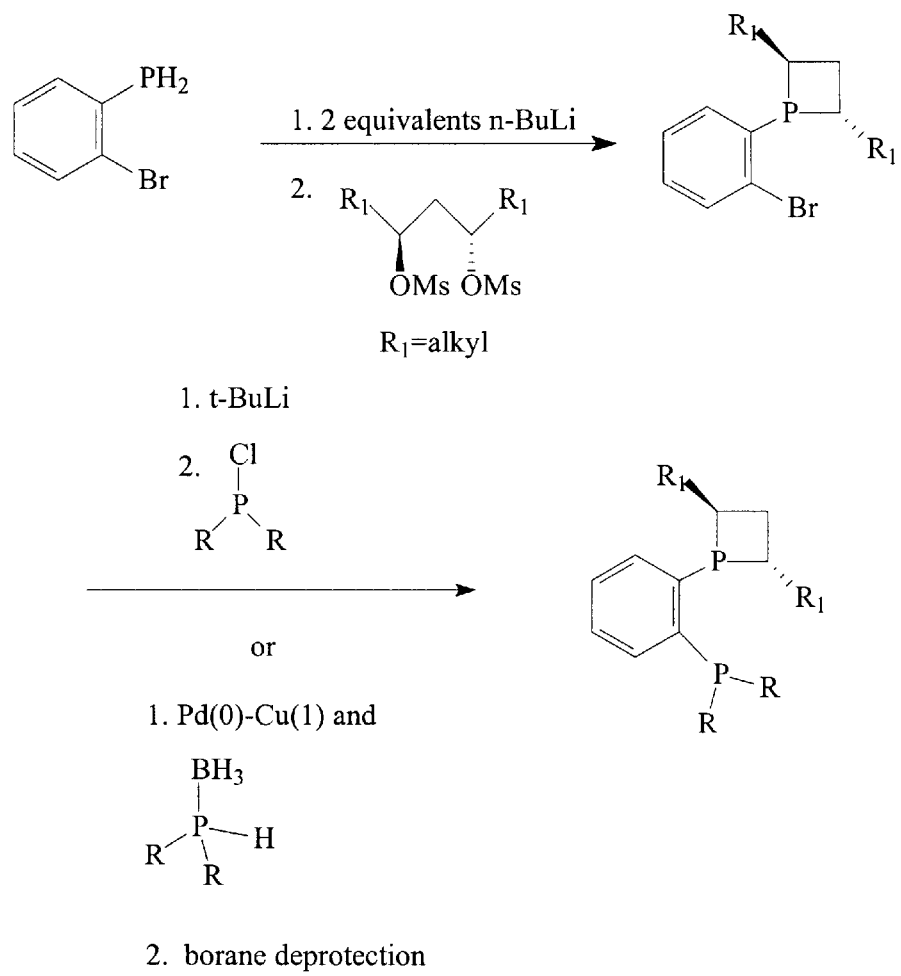
FIG. 12 shows a scheme for preparing another bisphosphine ligand.

Another compound can be synthesized via the route shown in FIG. 12, wherein R is t-butyl, isopropyl, adamantyl, (1,1)-dimethylpropane, (1,1-diethylbutane), c-$C_5H_9$, or c-$C_6H_{11}$, and Ms is mesylate.

Figure 13:
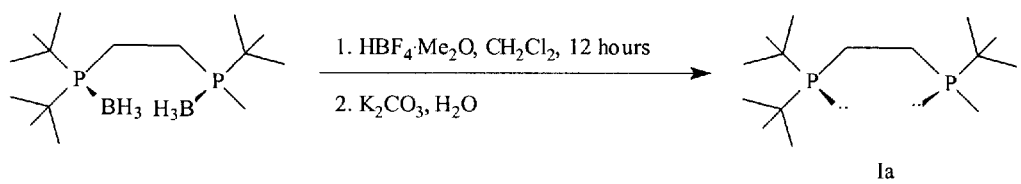
FIG. 13 shows a scheme for removing borane groups from an intermediate ligand to form a compound of Formula Ia.

Conditions can be used for borane removal or deprotection from the phosphorous atom of borane protected ligands, such as compounds shown in FIG. 9, that do not lead to racemization at the non-$C_2$-symmetric center to form compounds I, Ia, Ib, Ic, and IIa. The borane group can be removed by treating the phosphine borane ligand with $HBF_4.Me_2O$ followed by hydrolysis with $K_2CO_3$. For example, as shown in FIG. 13, the borane groups can be removed from an intermediate ligand to form a compound with the formula Ia.

Upon completion of borane removal, ligands of the general formulas I can be bound immediately to rhodium by reacting the ligand with $[Rh(norbomadiene)BF_4]_2$ to yield a catalyst with the Formula XIa:

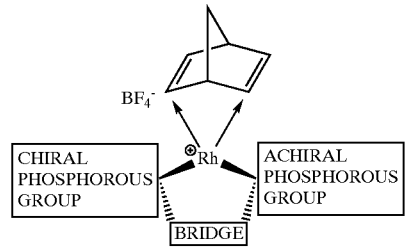

XIa wherein:
the achiral phosphorous group includes at least one achiral phosphorous atom having one bond to each of two identical atoms other than the bridge;

the chiral phosphorous group comprises at least one phosphorous atom, wherein the at least one phosphorous atom is chiral or the at least one phosphorous atom is bonded to a chiral substituent; and a Bridge is a —$(CH_2)_n$— where n is an integer from 1 to 12; a 1,2-divalent phenyl; or a 1,2-divalent substituted phenyl.

suitable transition metal, actinide, or lanthanide and corresponding anion can be used to form the metal/non-$C_2$ bisphosphine complex shown as compound XI. For example, the corresponding anion can alternatively be $PF_6^-$, $SbF_6^-$, $Otf^-$, or $ClO_4^-$.

Synthesis Route to BisP

Also shown in FIG. 9 is a synthesis method for the formation of BisP. Either enantiomer of compound IX can then easily be converted to either enantiomer of BisP, or the ligand Ia, as shown in FIG. 9. The difference in the synthesis of BisP and the ligand Ia is the use of either di-t-butylphosphine borane in the synthesis of ligand Ia or t-butylmethylphosphine borane in the synthesis of BisP, as the nucleophile that displaces the mesylate in the last step of the synthesis. In the synthesis of BisP, nucleophilic displacement creates yet another chiral center resulting in a reaction mixture that contains a 50:50 mixture of the chiral ligand and the meso ligand. The meso compound is easily separated from the chiral compound by column chromatography. In the case of the di-tert-butylphosphine borane addition, no further chiral centers are formed in the reaction so all of the material in the reaction mixture after addition is a single enantiomer chiral compound, Ia.

Asymmetric Transformations with Metal/Non-$C_2$-Synmetric Ligands

Metal/non-$C_2$-symmetric ligands of the general Formula XI can be used to catalyze hydrogenation and other asymmetric reactions. For example, compounds of the general Formula XI can also be used as catalysts in transformations including, but not limited to, hydroformylation, 7-allyl palladium coupling, hydrosilation, hydrocyanation, olefin metathesis, hydroacylation, and isomerization of allylamines.

In the case of asymmetric hydrogenation reactions, the metal/non-$C_2$-symmetric phospholanes can catalyze various substrates. For example, a complex represented by the Formula XIa, wherein the chiral group is

and the achiral group is

wherein R is t-butyl, isopropyl, adamantyl, (1,1-dimethylpropane), (1,1-diethylbutane), c-$C_5H_9$, or c-$C_6H_{11}$, can be used to catalyze substrates, such as enamides, enol esters, and succinates, with the general structural formula

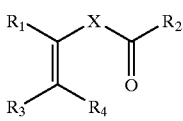

wherein X is N, O, or C; $R_1$ is an alkyl, a carboxylic acid derivative, a carboxylic ester, or a nitrile; $R_2$ is an alkyl, an acctyl derivative, or a carboxylic acid; and $R_3$ is an alkyl or hydrogen, and $R_4$ is an alkyl identical to the alkyl in $R_3$ or hydrogen.

Metal/non-$C_2$-symmetric compounds typically bond to a substrate to be catalyzed through the center, M, which is bound to a phosphorous atom of the chiral and achiral phosphorous groups, of a compound with the structural Formula XIb, its corresponding enantiomer, or solvates thereof XIb

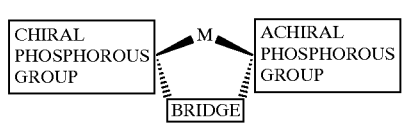

wherein:
R is an alkyl, fluoroalkyl, or perfluoroalkyl group each containing up to about 8 carbon atoms, an aryl group, a substituted aryl group, an aralkyl group, or a ring substituted aralkyl group;

a Bridge is a —$(CH_2)_n$— where n is an integer from 1 to 12; a 1,2-divalent phenyl; or a 1,2-divalent substituted phenyl; and M is a transition metal, an actinide, or a lanthanide.

A solvate of the Formula XIb includes compounds having one or more solvent molecules bonded to the M center. The solvent molecules include, but are not limited to, MeOH, THF, ethanol, isopropanol, acetonitrile, methylene chloride, benzene, toluene, water, ethyl acetate, dioxane, carbon tetrachloride, DMSO, DMF, DMF/water mixtures, supercritical carbon dioxide, alcohol/water mixtures or any other suitable solvent.

NON-$C_2$-SYMMETRIC LIGAND AND CATALYSTS GENERAL PROCEDURES

Materials. THF was distilled from sodium prior to use or THF (anhydrous, 99.9%) was used as needed from Aldrich Sure-Seal bottles supplied by Aldrich Chemical Company. Dichloromethane (anhydrous, 99.8%) and diethyl ether (anhydrous, 99.8%) were used as needed from Aldrich Sure-Scal bottles supplied by Aldrich Chemical Company. Methyl sulfoxide (DMSO, A.C.S. reagent, 99.9%), sodium borohydride (995), methanesulfonyl chloride (99.5%+), tert-butylmagnesium chloride (2.0 M diethyl ether), borane-methylsulfide complex (approximately 10–10.2 M), phosphorous trichloride (98%), lithium aluminum hydride (powder, 95%), and n-BuLi (2.5M hexanes) were obtained from Aldrich Chemical Company. N-chloroacetyl-(S)-(–)-4-benzyl-2-oxazolidinone was prepared according to literature procedures described in Tang, J. S., Verkade J. G. *J. Org. Chem.* 1996;61:8750–8754.

Nuclear Magnetic Resonance. 400 MHz $^1$H NMR, 100 MHz $^{13}$C NMR, and 162 MHz $^{31}$P NMR spectra were obtained on "Barton"—a Varian Unity+400 (Inova400 after Aug. 15, 2000) spectrometer equipped with an Auto Switchable 4-Nuclei PFG probe, two RF channels, and a SMS-100 sample changer by Zymark. Spectra were generally acquired near room temperature (21° C.), and standard autolock, autoshim, and autogain routines were employed. Samples are usually spun at 20 Hz for 1D experiments. $^1$H NMR spectra were acquired using 45-degree tip angle pulses, 1.0 second recycle delay, and 16 scans at a resolution of 0.25 Hz/point. The acquisition window was typically 8000 Hz from +18 to –2 ppm (Reference TMS @0 ppm), and processing was with 0.2 Hz line broadening. Typical acquisition time is 80 seconds. Regular $^{13}$C NMR spectra were acquired using 45-degree tip angle pulses, 2.0 second recycle delay, and 2048 scans at a resolution of 1 Hz/point. Spectral width was typically 25 KHz from +235 to –15 ppm (Reference TMS @0 ppm). Proton decoupling was applied continuously, and 2 Hz line broadening was applied during processing. Typical acquisition time is 102 minutes. 31 P NMR spectra were acquired using 45-degree tip angle pulses, 1.0 second recycle delay, and 64 scans at a resolution of 2 Hz/point. Spectral width was typically 48 KHz from +200 to –100 ppm (Reference 85% Phosphoric Acid (0 ppm). Proton decoupling was applied continuously, and 2 Hz line broadening was applied during processing. Typical acquisition time is 1.5 minutes.

High Performance Liquid Chromatography. High Performance Liquid Chromatography (HPLC) was performed on a series 1100 Hewlett Packard (now Agilent Technologies) instrument equipped with a manual injector, quaternary pump, and a UV detector. The LC was PC controlled using HP hesitation Plus Software. Reverse phase HPLC was performed with a 150×4.6 mm BDS-Hypersil-C18 column supplied by Keystone Scientific Incorporated. Reverse phase chiral HPLC was performed using a Chiracel OJ-R column supplied by Chiral Technologies. Normal Phase chiral HPLC was performed a Chiracel OD-H column supplied by Chiral Technologies.

EXAMPLE 1

Synthesis of di-tert-Butyl-phosphane Borane $PCl_3$ (3.94 g, 2.5 ml, 0.029 mole) was dissolved in 75 mL anhydrous THF in a 250-mL round bottom flask under $N_2$ and then cooled to 0° C. with an ice bath. The tert-butylmagnesium chloride (29 mL, 0.058 mole, 2.0 M in diethyl ether) was added dropwise via syringe, and then the reaction was stirred 1.5 hours at 0° C. Lithium aluminum hydride (1.1 g, 0.029 mole) was then delivered to the reaction as a dry powder in portions over 20 minutes. After the addition, borane methylsulfide (2.9 mL, 0.029 mole 10.0

M solution) was delivered via syringe. After stirring overnight, the reaction was cooled to 0° C. and then quenched cautiously with 150 mL 1N HCl. The reaction mixture was poured into a separatory funnel, and the organic layer was separated. The aqueous layer was extracted with 2×100 mL Et$_2$O and then the combined organics were dried over MgSO$_4$. The volatiles were then removed on a rotary evaporator at reduced pressure. The crude product was passed through a plug of silica gel using 3% ethyl acetate/hexane to yield the title compound with sufficient purity for subsequent chemistry. $^1$H NMR (400 MHz, CDCl$_3$) δ 0.0–0.9 (m, 3H), 1.28 (d, J$_{H-P}$=13.4 Hz, 18H), 3.65 (dm, J$_{H-P}$=351.2 Hz, 1H); $^{31}$P NMR (162 MHz, CDCl$_3$) δ 49.0 ppm (br m).

EXAMPLE 2

Synthesis of tert-Butyl-methyl-phosphane Borane

Dichloromethylphosphine (25 g, 0.214 mole) was poured out of an ampule into a 3-neck 1000-mL flask equipped with an addition funnel while blowing N$_2$ through the flask. Nitrogen degassed anhydrous Et$_2$O (350 mL) was immediately poured into the flask and then the flask was sealed with a septum. The solution was cooled to 0C and then borane methylsulfide (21.4 mL, 0.214 moles, 10.0 M solution) was delivered to the solution via syringe. After stirring for 20 minutes, tert-butylmagnesium chloride (107 mL, 0.214 mole, 2.0 M in ethyl ether) was delivered via the addition funnel over a period of one hour while maintaining the reaction solution at 0° C. During the addition, a white precipitate formed which persisted during stirring for 45 minutes after the addition. Lithium aluminum hydride was then delivered to the reaction as a dry powder in portions over 20 minutes while maintaining the reaction temperature at 0° C. After the addition the reaction was warmed to room temperature and then stirred overnight. It was then cooled to 0° C. and quenched cautiously with 400 mL 1N HCl. The organic layer was separated, and then the aqueous layer was extracted with 100 mL Et$_2$O. The combined organics were combined and washed with 1N HCl and brine and then dried over MgSO$_4$. Removal of the solvent in vacuo yielded 23.4 g/93% of the title compound with sufficient purity for subsequent chemistry. $^1$H NMR (400 MHz, CDCl$_3$) δ 0–0.8 (m, 3H), 1.17 (d, J$_{H-P}$=14.65 Hz, 9H), 1.28 (dd, J=4.64 Hz, J=5.86 Hz, 3H), 4.38 (dm, J$_{H-P}$=355.2 Hz, 1H); $^{31}$P NMR (162 MHz, CDCl$_3$) δ 12.0 (br m).

EXAMPLE 3

Synthesis of (S)-4-Benzyl-3-[2-((R)-tert-butyl-methyl-phosphanyl)-ethanoyl]-oxazolidin-2-one and (S)-4-Benzyl-3-[2-((S)-tert-butyl-methyl-phosphanyl)-ethanoyl]-oxazolidin-2-one N-Chloroacetyl-(S)-(−)-4-benzyl-2-oxazolidinone (6.39 g, 0.0254 mole) was placed in a 250-mL round bottom flask. (+/−)-tert-butyl-methyl-phosphane borane was added to the flask along with 75 mL DMSO. Potassium carbonate (17.5 g, 0.127 mole) was added in one portion and the reaction was placed under N$_2$. The reaction was heated to 55° C. in an oil bath and stirred for one hour. The resulting solution was red and K$_2$CO$_3$ was not completely dissolved in solution. The reaction was cooled to room temperature and then was poured into 500 mL 1N HCl which had been chilled to 0° C. Ethyl acetate (300 mL) was added and the biphasic solution was shaken briskly in a separatory funnel. The organic layer was separated and then the aqueous layer was extracted with 100 mL ethyl acetate. The combined organic layers were then washed successively with distilled water and then brine. The organic layer was dried over MgSO$_4$ and the solvent was removed in vacuo. The crude white oily product was triturated with 2×75 mL warm hexane to remove excess phosphine and then the resulting white solid was dissolved in 30 mL hot ethyl acetate and allowed to cool to room temperature. Upon cooling, crystals formed. The crystals were collected on filter paper and then washed with 30 mL hexane. Crystals then formed in the filtrate. The diastereomeric ratio of the crystals on the filter paper was 92 ((S,R) isomer):8 ((S,S) isomer) and they weighed 1.17 g. After collecting the crystals from the filtrate on filter paper and washing with hexane it was found that the diastereomeric ratio of these crystals was 8 ((S,R) isomer):92 ((S,S) isomer) and then weighed 1.20 g. Successive recrystallization of both diastereomers with EtOAc/hexane yielded compounds with diastereomeric purity exceeding 99%. It is also possible to separate the (S,R) and (S,S) diastereomers via column chromatography over silica gel (15%/ ethyl acetate, hexane) collecting the (S,R) isomer at R$_f$=0.38 and the (S,S) isomer at R$_f$=0.28. Stereochemistry of the chirogenic phosphorous atom of each diastereomer was assigned by analogy using a comparison of elution orders of the enantiomers of Bis-P boranes made from this route with the elution orders of Bis-P boranes described in Imamoto, T. et al., supra., 1998.

(S)-4-Benzyl-3-[2-((R)-tert-butyl-methyl-phosphanyl)-ethanoyl]-oxazolidin-2-one $^1$H NMR (400 MHz, CDCl$_3$) δ −0.2–0.8 (m, 3H), 1.22 (d, J$_{H-P}$=14.7 Hz, 9H), 1.43 (d, J$_{H-P}$=9.89 Hz, 3H), 2.80 (m, 2H), 3.36 (dd, J=3.38 Hz, J=13.5 Hz, 1H), 4.15 (dd, J=2.17 Hz, J=8.92 Hz, 1H), 4.26 (dd, J=8.68 Hz, J=8.68 Hz, 1H), 4.34 (dd, J=9.16 Hz, J=12.18 Hz, 1H), 4.68 (m, 1H), 7.22–7.36 (m, 5H); $^{13}$C NMR (100 MHz, CDCl$_3$) δ 6.6 (d, J$_{C-P}$=33.6 Hz), 24.9, 28.1 (d, J$_{C-P}$=20.6 Hz), 38.2, 56.1, 66.3, 127.4, 129.2 (d, J$_{C-P}$=46.5 Hz), 135.4, 154.0, 167.5; $^{31}$P NMR (162 MHz, CDCl$_3$) δ 27.8 (br m).

(S)-4-Benzyl-3-[2-((S)-tert-butyl-methyl-phosphanyl)-ethanoyl]-oxazolidin-2-one:

$^1$H NMR (400 MHz, CDCl$_3$) δ −0.2–0.8 (m, 3H), 1.24 (d, J$_{H-P}$=14.47 Hz, 9H), 1.45 (d, J$_{H-P}$=9.89 Hz, 3H), 2.76 (dd, J=10.6 Hz, J=10.6 Hz, 1H), 3.21 (dd, J=13.3 Hz, J=13.3 Hz, 1H), 3.50 (dd, J=3.6 Hz, J=13.8 Hz, 1H), 3.94 (dd, J=10.1 Hz, J=12.8 Hz, 1H), 4.14–4.22 (m, 2H), 4.71 (m, 1H), 7.23–7.28 (m, 3H), 7.31–7.35 (m, 2H); $^{13}$C NMR (100 MHz, CDCl$_3$) δ 8.0 (d, J$_{C-P}$=30 Hz), 24.9, 27.9 (d, J$_{C-P}$=22 Hz), 29.0 (d, J$_{C-P}$=30 Hz), 38.0, 55.8, 66.2, 127.3, 129.0, 136.0, 154.0, 168.0; $^{31}$P NMR (162 MHz, CDCl$_3$) δ 31.2 (br m).

EXAMPLE 4

Synthesis of (R)-2-(tert-Butyl-methyl-phosphanyl)-ethanol (S)-4-Benzyl-3-[2-((R)-tert-butyl-methyl-phosphanyl)-ethanoyl]-oxazolidin-2-one was dissolved in 60 mL anhydrous THF and then cooled to 0° C. in a 250-mL round bottom flask. NaBH$_4$ was added in one portion along with 15 mL distilled water. The reaction foamed after addition and when foaming was complete the reaction was warmed to room temperature and stirred overnight whereupon the reaction was quenched with 50 mL 2N HCl. The reaction was poured into a separatory funnel and 30 mL ethyl acetate was added. The organic layer was separated after shaking and then the aqueous layer was extracted with 2×50 mL ethyl acetate. The organic layers were combined and dried over MgSO$_4$ and then the volatiles were removed in vacuo. The crude product was passed through a plug of silica gel using 25% ethyl acetate/hexane and after removing the volatiles in vacuo, 1.651 g/97.1% of the title compound was isolated. The (S) isomer can be synthesized via the same procedure starting from (S)-4-benzyl-3-[2-((S)-tert-butyl-methyl-phosphanyl)-ethanoyl]-oxazolidin-2-one.

$^1$H NMR (400 MHz, CDCl$_3$) δ 1.14 (d, J$_{H\text{-}P}$=13.74 Hz, 9H), 1.25 (d, J$_{H\text{-}P}$=9.9 Hz, 3H), 1.81–1.92 (m, 2H), 2.42 (br s, 1H); 3.92 (dt, J=15.2 Hz, J=6.3 Hz, 2H); $^{13}$C (100 MHz, CDCl$_3$) δ 6.3 (d, J$_{C\text{-}P}$=35.1 Hz), 24.6 (d, J=32.1 Hz), 24.9, 27.2 (d, J$_{C\text{-}P}$=35.1 Hz), 57.8; $^{31}$P (162 MHz, CDCl$_3$) δ 23.2 (br m).

EXAMPLE 5

Synthesis of Methanesulfonic Acid 2-((R)-tert-Butyl-methyl-phosphanyl Borane)-ethyl Ester The (R)-2-(tert-butyl-methyl-phosphanyl)-ethanol (1 27 g, 6.957 mmole) was dissolved in 10 mL pyridine and cooled to 0° C. Methanesulfonyl chloride (0.59 mL, 7.65 mmole) was added dropwise via syringe. After one hour white salts had precipitated from the reaction solution. The reaction was then quenched with 50 mL distilled water. The reaction mixture was poured into a separatory funnel and the aqueous layer was extracted with 2×50 mL Et$_2$O. The combined organics were dried over MgSO$_4$ and then the volatiles were removed in vacuo yielding 1.553 g/93% of the mesylate product which was subjected to no further purification. The (S) isomer can be synthesized via the same procedure starting from (S)-2-(tert-butyl-methyl-phosphanyl)-ethanol. $^1$H NMR (400 MHz, CDCl$_3$) δ 0.0–0.8 (br m), 1.17 (d, J$_{H\text{-}P}$=14.2 Hz, 9H), 1.30 (d, J$_{H\text{-}P}$=9.9 Hz, 3H), 1.90 (br s, 1H), 2.08 (dt, J=10.9 Hz, J=7.5 Hz, 2H), 3.05 (s, 3H), 4.41–4.59 (m, 2H); $^{31}$P NMR (162 MHz, CDCl$_3$) δ 25.5 (br m).

EXAMPLE 6

Synthesis of (R,R)-1,2-Bis(tert-butyl-methyl-phosphanyl Borane) Ethane

Methanesulfonic acid 2-((R)-tert-butyl-methyl-phosphanyl borane)-ethyl ester (536 mg, 2.232 mmole) was dissolved in 7 mL anhydrous THF in a 50-mL round bottom flask under N$_2$. The solution was cooled to −78° C. with a dry ice/acetone bath with stirring. In a separate 25-mL round bottom flask was dissolved (+/−)-tert-butyl-methyl-phosphane borane. This solution was placed under N$_2$ and then cooled to −78° C. n-BuLi (1.07 mL, 2.678 mmole, 2.5 M in hexane) was added dropwise via syringe to the (+/−)-tert-butyl-methyl-phosphane borane solution. The reaction was stirred for 20 minutes at −78° C. and then the solution was taken up in a syringe and delivered to the mesylate solution over 30 seconds. The reaction was stirred 20 minutes at −78° C. and then warmed to room temperature and stirred overnight. TLC (25% ethyl acetate/hexane) showed two products with R$_f$=0.49 (meso Bis-P) and R$_f$=0.38 (Bis-P). Column chromatography over silica gel eluting first with 7% ethyl acetate/hexane and increasing the gradient eventually to 25% ethyl acetate/hexane yielded 130 mg/44.5% meso compound and 147 mg/50.3% Bis-P (>99% e.e. of the (R,R) isomer). The (S,S) isomer can be synthesized via the same procedure starting from Methanesulfonic acid 2-((S)-tert-butyl-methyl-phosphanyl borane)-ethyl ester. Enantiomeric purity was determined by chiral HPLC using a Chiracel OD-H column (10 mm, 4.6×250 mm), mobile phase Hexanes:IPA:TFA 95:5:0.1, flow rate of 0.5 mL/min, and RI detection at 1/16 range. The (S,S) isomer was observed at 17.9 minutes and the (R,R) isomer was observed at 12.0 minutes. Spectral data was identical to that described in Imamoto T., et al., supra., 1998.

EXAMPLE 7

Synthesis of 1-(di-tert-Butyl-phosphanyl Borane)-((R)-2-tert-butyl-methyl-phosphanyl Borane) Ethane Methanesulfonic acid 2-((R)-tert-butyl-methyl-phosphanyl borane)-ethyl ester (660 mg, 2.75 mmole) was dissolved in 7 mL anhydrous THF in a 50-mL round bottom flask under N$_2$. The solution was cooled to −78° C. with a dry ice/acetone bath. In a separate 25-mL round bottom flask was dissolved di-tert-butyl-phosphane borane (528 mg, 3.30 mmole). This solution was placed under N$_2$ and then cooled to −78° C. n-BuLi (1.32 mL, 3.30 mmole, 2.5 M in hexane) was added dropwise via syringe to the di-tert-butyl-phosphane borane solution. The reaction was stirred for 20 minutes at −78° C. and then the solution was taken up in a syringe and delivered to the mesylate solution over 30 seconds. The reaction was stirred 20 minutes at −78° C. and then warmed to room temperature and stirred overnight. TLC (25% ethyl acetate/hexane) showed title product with R$_f$=0.53. Column chromatography over silica gel (10% ethyl acetate/hexane) yielded 370 mg/44% of the title compound. The (S) isomer can be synthesized via the same procedure starting from Methanesulfonic acid 2-((S)-tert-butyl-methyl-phosphanyl borane)-ethyl ester. $^1$H NMR (400 MHz, CDCl$_3$) δ −0.2–0.8 (br m, 3H), 1.05–1.30 (br m, 30H), 1.50–1.70 (br m, 2H), 1.75–2.05 (br m, 2H), $^{31}$P NMR (162 MHz, CDCl$_3$) δ 30.0 (br m), 47.0 (br, m).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

What is claimed is:

1. A non-C$_2$ symmetric bisphosphine ligand having structural formula:

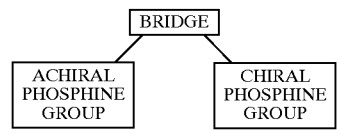

wherein the bridge is a 1,2-divalent phenyl, a 1,2-divalent substituted phenyl, or a —(CH$_2$)$_n$— in which n is an integer from 1 to 12;

the achiral phosphine group is

in which R is t-butyl, isopropyl, adamantyl, 1,1-dimethylpropane, 1,1-diethylbutane, or c-C$_5$H$_9$; and the chiral phosphine group includes a three-coordinated phosphorous atom which is bonded to the bridge and to two carbon atoms, the two carbon atoms and the phosphorus atom not being part of a ring system.

2. The non-C$_2$ symmetric bisphosphine ligand of claim 1, wherein the bridge is —(CH$_2$)$_n$— and n is an integer from 1 to 12.

3. The non-C$_2$ symmetric bisphosphine ligand of claim 1, wherein R is t-butyl.

4. The non-C$_2$ symmetric bisphosphine ligand of claim 2, wherein n is an integer from 1 to 2.

5. The non-C$_2$ symmetric bisphosphine ligand of claim 4, wherein R is t-butyl.

6. A non-C$_2$ symmetric bisphosphine ligand having structural formula:

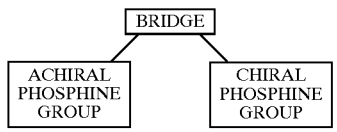

wherein the bridge is a 1,2-divalent phenyl, a 1,2-divalent substituted phenyl, or a —(CH$_2$)$_n$— in which n is an integer from 1 to 12;

the achiral phosphine group includes a three-coordinated, achiral phosphorous atom which is bonded to the bridge and to two carbon atoms, the two carbon atoms and the phosphorus atom not being part of a ring system; and the chiral phosphine group is

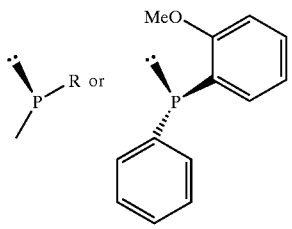

or corresponding enantiomers, in which R is t-butyl, isopropyl, 1,1-dimethylpropane, 1,1-diethylbutane, c-C$_5$H$_9$, or c-C$_6$H$_{11}$.

7. The non-C$_2$ symmetric bisphosphine ligand of claim 6 wherein the bridge is —(CH$_2$)$_n$— and n is an integer from 1 to 12.

8. The non-C$_2$ symmetric bisphosphine ligand of claim 7 wherein the chiral phosphine group is

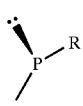

or its corresponding enantiomer and R is t-butyl, isopropyl, 1,1-dimethylpropane, 1,1-diethylbutane, c-C$_5$H$_9$, or c-C$_6$H$_{11}$.

9. The non-C$_2$ symmetric bisphosphine ligand of claim 8, wherein R is t-butyl.

10. The non-C$_2$ symmetric bisphosphine ligand of claim 7, wherein n is an integer from 1 to 2.

11. The non-C$_2$ symmetric bisphosphine ligand of claim 10 wherein the chiral phosphine group is

or its corresponding enantiomer and R is t-butyl, isopropyl, 1,1-dimethylpropane, 1,1-diethylbutane, c-C$_5$H$_9$, or c-C$_6$H$_{11}$.

12. The non-C$_2$ symmetric bisphosphine ligand of claim 11 wherein R is t-butyl.

13. A compound having the structural formula:

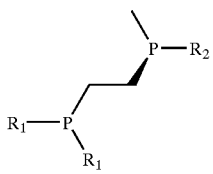

or its corresponding enantiomer, in which R$_1$ is t-butyl, isopropyl, adamantyl, 1,1-dimethylpropane, 1,1-diethylbutane, c-C$_5$H$_9$, or c-C$_6$H$_{11}$, and R$_2$ is t-butyl, isopropyl, 1,1-dimethylpropane, 1,1-diethylbutane, c-C$_5$H$_9$ or c-C$_6$H$_{11}$.

14. A compound having the structural formula:

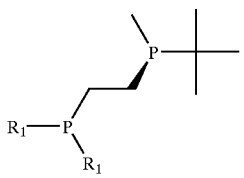

or its corresponding enantiomer, in which R$_1$ t-butyl, isopropyl, adamantyl, 1,1-dimethylpropane, 1,1-diethylbutane, c-C$_5$H$_9$, or c-C$_6$H$_{11}$.

15. A compound having the structural formula:

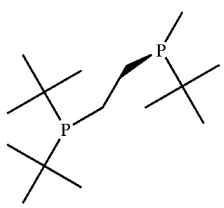

or its corresponding enantiomer.

16. A non-C$_2$ symmetric bisphosphine ligand having structural formula:

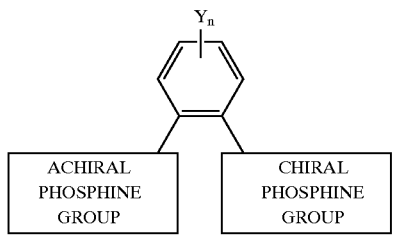

wherein the achiral phosphine group is

in which R is t-butyl, isopropyl, adamantyl, 1,1-dimethylpropane, 1,1-diethylbutane, c-C$_5$H$_9$, or c-C$_6$H$_{11}$;

the chiral phosphine group includes a three-coordinated phosphorous atom which is bonded to the bridge and to two carbon atoms, the two carbon atoms and the phosphorus atom not being part of a ring system; and each Y is independently halogen, alkyl, alkoxy, aryl, aryloxy, nitro, amino, vinyl, substituted vinyl, alkynyl, or sulfonic acid, and n is an integer from 0 to 4.

17. A non-C$_2$ symmetric bisphosphine ligand having structural formula:

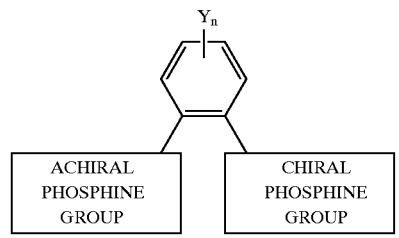

wherein the achiral phosphine group includes a three-coordinated, achiral phosphorous atom which is bonded to the bridge and to two carbon atoms, the two carbon atoms and the phosphorus atom not being part of a ring system;

the chiral phosphine group is

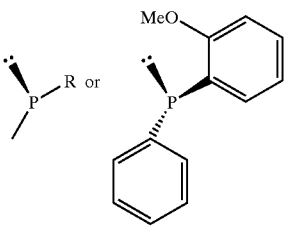

or corresponding enantiomers, in which R is t-butyl, isopropyl, adamantyl, 1,1-dimethylpropane, 1,1-diethylbutane, c-C$_5$H$_9$, or c-C$_6$H$_{11}$; and each Y is independently halogen, alkyl, alkoxy, aryl, aryloxy, nitro, amino, vinyl, substituted vinyl, alkynyl, or sulfonic acid and n is an integer from 0 to 4.

* * * * *